United States Patent [19]

LeCacheur et al.

[11] Patent Number: 5,326,796
[45] Date of Patent: Jul. 5, 1994

[54] USE OF AN ARYLSULPHONYLURETHANE AS FILM FORMING RESIN IN NITROCELLULOSE NAIL VARNISHES, NEW ARYLSULPHONYLURETHANES AND NEW NITROCELLULOSE NAIL VARNISHES

[75] Inventors: Maryse LeCacheur, Bergerac; Eric Wimmer, Saint Jaen de Braye; Vincent Mutterer, Stasbourg, all of France

[73] Assignee: Societe Nationale des Poudres et Explosifs, Paris, France

[21] Appl. No.: 57,082

[22] Filed: May 4, 1993

[30] Foreign Application Priority Data

May 6, 1992 [FR] France .................. 92 05560

[51] Int. Cl.⁵ .................. C08L 1/18; C07C 265/12
[52] U.S. Cl. .................. 524/31; 528/69; 524/716; 524/840; 560/29
[58] Field of Search .................. 528/69, 716, 840; 560/29; 524/31

[56] References Cited

U.S. PATENT DOCUMENTS

| | | | |
|---|---|---|---|
| 3,607,935 | 11/1971 | Hilmer et al. | 564/39 |
| 3,687,934 | 8/1972 | Dietrich et al. | 560/12 |
| 3,787,491 | 1/1974 | Bretschndier et al. | 564/43 |
| 3,864,294 | 2/1975 | Busch, Jr. | 106/266 |
| 3,925,527 | 12/1975 | Kleimann et al. | 264/53 |
| 3,933,894 | 1/1976 | Stephens | 560/13 |
| 4,224,418 | 9/1980 | Dieterich et al. | 528/69 |
| 4,513,127 | 4/1985 | Jacobine | 526/194 |
| 4,661,542 | 4/1987 | Gilch et al. | 524/59 |
| 4,772,329 | 9/1988 | Lühmann et al. | 524/32 |
| 4,820,509 | 4/1989 | Yamazaki et al. | 424/61 |
| 5,008,311 | 4/1991 | Janoski | 524/705 |

FOREIGN PATENT DOCUMENTS

| | | |
|---|---|---|
| 449488 | 10/1991 | European Pat. Off. . |
| 3919747 | 12/1989 | Fed. Rep. of Germany . |
| 2326414 | 4/1947 | France . |
| 1239917 | 7/1960 | France . |
| 1471089 | 5/1966 | France . |
| 1340297 | 1/1970 | France . |
| WO9012829 | 11/1990 | PCT Int'l Appl. . |

*Primary Examiner*—John Kight, III
*Assistant Examiner*—Jeffrey Culpeper Mullis
*Attorney, Agent, or Firm*—Bucknam and Archer

[57] ABSTRACT

The present invention lies in the field of nitrocellulose nail varnishes and its subject is the use of an arylsulphonylurethane as film forming resin in these varnishes, which makes it possible in particular to avoid the release of formaldehyde, a carcinogenic compound which is formed when an arylsulphonamide-formaldehyde resin is employed.

Another subject of the invention is new poly(arylsulphonylurethanes) containing from 2 to 5 arylsulphonylurethane groups and possessing a molecular mass of between 450 and 1500.

8 Claims, No Drawings

USE OF AN ARYLSULPHONYLURETHANE AS FILM FORMING RESIN IN NITROCELLULOSE NAIL VARNISHES, NEW ARYLSULPHONYLURETHANES AND NEW NITROCELLULOSE NAIL VARNISHES

FIELD OF THE INVENTION

The present invention relates to the field of colourless or coloured nitrocellulose nail varnishes. It relates more particularly to the field of nail varnishes consisting essentially of nitrocellulose, a film forming resin, a plasticizer, a gelling agent and a solvent-diluent system. It also relates to new arylsulphonylurethanes.

A coloured nitrocellulose nail varnish is generally obtained by mixing a colourless thixotropic nitrocellulose antisedimenting base, which is in fact a colourless nail varnish, with one or more pigments or dyes or with a colouring base which may be obtained, for example, by mixing an antisedimenting base with one or more pigments.

The colourless thixotropic nitrocellulose antisedimenting base is, according to a traditional process, obtained by mixing a colourless thixotropic nitrocellulose gel and a nonthixotropic colourless base, preferably in the presence of a small quantity of an acid such as phosphoric acid or citric acid to promote the thixotropy of the antisedimenting base.

The nonthixotropic colourless base consists of nitrocellulose, a film forming resin, a plasticizer and solvents and/or diluents.

The colourless thixotropic nitrocellulose gel consists of nitrocellulose, a gelling agent, a plasticizer, solvents and/or diluents and, optionally, a wetting agent.

The main characteristics which nail varnishes must exhibit are well known to a person skilled in the art. In particular, they must not present a health risk.

The film forming resin employed in nitrocellulose nail varnishes makes it possible to impart body to the varnish, in other words to increase the solids content after evaporation to dryness, so that the quantity of binder which is deposited after evaporation is as large as possible. The resin also contributes to the gloss of the varnish and to adhesiveness to the nail.

On an industrial scale, arylsulphonamide-formaldehyde resins, which offer many advantages, are practically the only ones employed. However, they have the major disadvantage of releasing formaldehyde in the course of time. Now, it has been found that formaldehyde is a carcinogenic compound and, as a result, persons skilled in the art are searching for a new film forming resin compatible with the other constituents of nitrocellulose nail varnishes, which has the advantages of the arylsulphonamide-formaldehyde resins employed hitherto, but which would not have the abovementioned disadvantage.

BACKGROUND OF THE INVENTION

The state of the art proposes a number of solutions.

Patent Application PCT WO 90/12829 describes the use of epoxysulphonamide resins in compositions for cosmetics and especially in nitrocellulose nail varnishes. However, the cost of these resins rules out an industrial application.

French Patent Application FR 2,421,604 describes nitrocellulose nail varnishes comprising, as product replacing the arylsulphonamide-formaldehyde resins, a composition including sucrose benzoate by itself or mixed with methyl methacrylate, sucrose acetate isobutyrate and a phthalate, an adipate or an organic phosphate. This solution therefore requires the preliminary preparation of a premix, and this makes the process more complex and costly.

The known solutions are therefore not wholly satisfactory.

SUMMARY OF THE INVENTION

The crux of the present invention resides in replacing arylsulphonamide-formaldehyde resins in nitrocellulose nail varnishes, a solution which does not exhibit the abovementioned disadvantages of the solutions proposed so far.

Unexpectedly, applicants have found that the use of arylsulphonylurethanes as film forming resin in nitrocellulose nail varnishes instead of arylsulphonamide-formaldehyde resins make it possible, simply and inexpensively, to obtain nail varnishes which have closely related and satisfactory properties, without the formation of formaldehyde in the course of time.

"Arylsulphonylurethanes" are intended to mean organic compounds containing one - mono(arylsulphonylurethanes)- or a number of - poly(arylsulphonylurethanes)-arylsulphonylurethane group(s) of structure $ArSO_2NH-C(=O)-O-$, Ar denoting an aromatic group.

Many mono(arylsulphonylurethanes) are known. For example U.S. Pat. No. 4,287,083 describes the use of acyloin urethanes, especially of

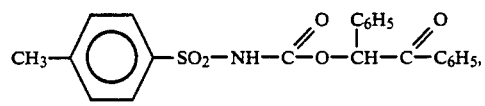

as radical polymerization photoinitiators.

Other mono(arylsulphonylurethanes) are known as plant-protection derivatives or as intermediates in the synthesis of medications.

U.S. Pat. No. 4,513,127 teaches, furthermore, the use of poly(arylsulphonylurethanes) as accelerators for the polymerization of crosslinkable acrylic monomers. This patent describes di(arylsulphonylurethanes) which have a silane or organosiloxane polymer backbone with a mass of 1860 or 5360.

One subject of the present invention is therefore new poly(arylsulphonylurethanes) containing from 2 to 5, that is to say 2, 3, 4 or 5, arylsulphonylurethane groups, which have a molecular weight of between 450 and 1500, and particularly preferably those in which the aryl group is the para-tolyl group

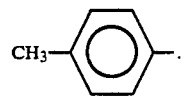

According to a preferred embodiment the poly(arylsulphonylurethanes) according to the invention are characterised in that they correspond to the general formula (II)

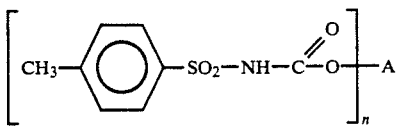

in which n denotes an integer such that $2 \leq n \leq 5$ and A denotes an organic radical which is divalent when $n=2$, trivalent when $n=3$, tetravalent when $n=4$ and pentavalent when $n=5$, which is the backbone of polyols of structure

which are chosen from the group consisting of:
polymethylene glycols, for example glycol and trimethylene glycol,
polyoxyalkylene glycols, for example dioxyethylene glycol, trioxyethylene glycol, dioxypropylene glycol and trioxypropylene glycol,
polyethertriols and polyethertetraols,
glycerol and xylitol,
trimethylolalkanes, for example trimethylolpropane.

As polyethertriols, preference is given to those corresponding to the general formulae:

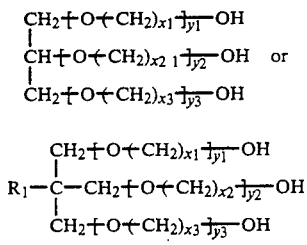

in which
$x_1$, $x_2$ and $x_3$, which are identical or different, preferably identical, denote 1, 2, 3 or 4,
$y_1$, $y_2$ and $y_3$, which are identical or different, denote 0, 1, 2, 3, 4, 5 or 6 provided that $y_1$, $Y_2$ and $y_3$ are not simultaneously zeros,
$R_1$ denotes hydrogen or a linear or branched alkyl chain containing 1 to 8 carbon atoms, or an alkyl chain containing 1 to 8 carbon atoms which is substituted by at least one alkoxy radical.

Preferably, $x_1=x_2=x_3=2$ and $y_1$, $y_2$ and $y_3$ denote 2 or 3.

As polyethertetraols, preference is given to those corresponding to the general formula

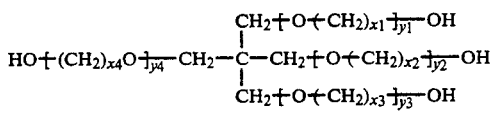

in which
$x_1$, $x_2$, $x_3$ and $x_4$, which are identical or different, preferably identical, denote 1, 2, 3 or 4,
$y_1$, $y_2$, $y_3$ and $y_4$, which are identical or different, denote 0, 1, 2, 3, 4, 5 or 6 provided that $y_1$, $y_2$, $y_3$ and $y_4$ are not simultaneously zero.

Preferably, $x_1=x_2=x_3=x_4=2$ and $y_1$, $y_2$, $y_3$ and $y_4$ denote 1, 2 or 3.

The arylsulphonylurethanes can be obtained, for example, by reaction of an arylsulphonyl isocyanate with an alcohol.

The poly(arylsulphonylurethanes) according to the invention can be obtained by reaction of Ar—SO$_2$—NCO with a polyol, Ar denoting an aromatic group, optionally heterocyclic, for example a phenyl or naphthyl group, unsubstituted or substituted, for example, by a $C_1$-$C_4$ alkyl chain. Particularly preferably, Ar denotes the para-tolyl group. Since each hydroxyl of the polyol reacts with one isocyanate functional group, this makes it possible to obtain a number of arylsulphonylurethane groups which is identical with the number of hydroxyl functional groups in the polyol.

The starting materials, especially

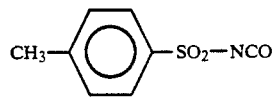

and most of the abovementioned polyols

are conventional and relatively inexpensive industrial products. Furthermore, the reaction between the isocyanate and the alcohol is simple to carry out and low in cost.

The poly(arylsulphonylurethanes) according to the invention are therefore very cheap products and are very easily accessible.

During the reaction between the arylsulphonyl isocyanate and the alcohol, according to a preferred embodiment, the reaction mixture is stirred and the temperature is controlled and is varied as a function of the viscosity of the mixture, in order to avoid an untimely solidification.

It is also preferred to work under an inert gas, for example nitrogen.

According to another embodiment, the work is done without solvent, but it is also possible to work in a solvent medium, for example dimethylformamide (DMF), when the mixture is very viscous.

According to another preferred embodiment, the isocyanate is added gradually to the alcohol placed in the reactor and the operation is carried out with an NCO/OH functional group ratio of between 0.99 and 1.00. The end of reaction can be checked by determining the residual isocyanate functional groups in the reaction mixture.

The kinetics of the reaction can also be accelerated by operating in the presence of a conventional catalyst for isocyanate-alcohol reactions.

This process is very simple to carry out, it being possible for the required product, which is generally a solid or viscous liquid at room temperature, to be obtained directly without any additional stage of concentration and/or purification, merely by mixing the two starting compounds.

A further subject of the present invention is new nitrocellulose nail varnishes, more precisely those consisting essentially of nitrocellulose, a film forming resin, a plasticizer, a gelling agent and a solvent-diluent system. These varnishes are characterised in that the film forming resin includes an arylsulphonylurethane.

The use of the singular in referring to the constituents should not be taken in a restrictive sense, it being possible for nitrocellulose to be a mixture of various nitrocelluloses, the resin a mixture of a number of resins, and so on.

The expression "essentially consisting of" means that the constituents referred to are constituents whose presence is indispensable and that they are predominant throughout the nail varnish, which may, furthermore, include usual additives which may vary depending on the various types of varnish, such as pigments, dyes, wetting agents, swelling agents, Oriental essences and agents which absorb UV radiation.

The film forming resin which, according to the invention, includes an arylsulphonylurethane may also include one or a number of resins employed hitherto, for example an arylsulphonamide-formaldehyde resin, an alkyd resin or an acrylic resin. However, the film forming resin preferably consists solely of one or more arylsulphonylurethanes.

It is preferred to employ, as arylsulphonylurethanes, the abovementioned new arylsulphonylurethanes according to the invention and, in particular, the abovementioned preferred subgroups of these compounds.

However, when a mono(arylsulphonylurethane) is nevertheless employed, it is preferred to employ those of general formula (I)

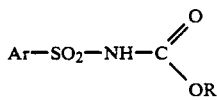

in which

Ar has the abovementioned meaning,

R denotes either a linear or branched alkyl or cycloalkyl group or an alkyl or cycloalkyl group substituted by at least one alkoxy (for example methoxy, ethoxy, propoxy or butoxy) or polyoxyalkyl group. R preferably contains from 2 to 12 carbon atoms.

According to a preferred embodiment, the mono(arylsulphonylurethanes) of formula (I) have a molecular weight of between 230 and 350.

In general, the mono(arylsulphonylurethanes), especially those mentioned above of formula (I), can be obtained as mentioned above in the case of poly(arylsulphonylurethanes) according to the invention, but by replacing the polyol with a monoalcohol.

According to the invention the nitrocellulose may include any nitrocellulose employed generally as a film forming agent in conventional nail varnishes. Use is made, for example, of "½second" nitrocellulose or "¼second" nitrocellulose according to the U.S. standard, or E33 and E27 according to the European standard, with a molecular mass of 36,000 and 26,000 respectively. A mixture of various nitrocelluloses in any proportions may be employed.

The function of the plasticizer is to decrease the hardness of the film by imparting flexibility to it. Some esters, ketones and ethers can be employed for plasticizing a nitrocellulose varnish. The following compounds may be mentioned as examples of plasticizers which can be employed for implementing the present invention, without any limitation being implied by this list: diethyl adipate, dibutyl adipate, diisobutyl adipate, dihexyl adipate, dicapryl adipate, di(2-ethylhexyl) adipate, diisooctyl adipate, dinonyl adipate, octyl decyl adipate, isooctyl isodecyl adipate, didecyl adipate, diisodecyl adipate, isodecyl octyl adipate, polypropylene glycol adipate, di(methoxyethyl) adipate, di(ethoxyethyl) adipate, di(butoxyethyl)adipate, di(butoxyethoxyethyl) adipate, dimethyl phthalate, diethyl phthalate, dipropyl phthalate, dibutyl phthalate, diisobutyl phthalate, dihexyl phthalate, butyl octyl phthalate, butyl isodecyl phthalate, butyl isohexyl phthalate, lauryl isohexyl phthalate, dioctyl phthalate, diisooctyl phthalate, dicapryl phthalate, di(2-ethylhexyl) phthalate, dinonyl phthalate, di(ethyldecyl) phthalate, isooctyl isodecyl phthalate, didecyl phthalate, ethylhexyl decyl phthalate, butyl ethylhexyl phthalate, bismethoxyethyl phthalate, (2-ethylhexyl) triiphenyl phosphate, modified triaryl phosphate, triiphenyl phosphate, isodecyl diphenyl phosphate, benzyl benzoate, butyl acetylricinoleate, glyceryl acetylricinoleate, butyl glycolate, butyl stearate, diethyl citrate, tributyl citrate, tributyl acetylcitrate, tri-2-ethylhexyl acetylcitrate, dibutyl tartrate and mixtures of these compounds.

The preferred gelling agents are organophilic clays of amine-modified montmorillonite type. All those described in U.S. Pat. No. 3,422,185 may be mentioned, especially those marketed by the National Lead Company under the registered mark "Bentone".

The solvent-diluent system may be aromatic or non-aromatic.

In the case of a nonaromatic system, this consists, for example, of aliphatic esters such as butyl acetate and ethyl acetate, which are employed as solvents, and of aliphatic alcohols such as isopropanol and butanol, which are employed as diluents.

In the case of an aromatic system this generally consists of one or a number of the abovementioned aliphatic esters and alcohols mixed with an aromatic hydrocarbon, for example toluene.

According to a preferred alternative form of the invention the nail varnish consists of 5% to 20% by weight of nitrocellulose, 1% to 20% by weight of an arylsulphonylurethane resin, 0.1% to 5% by weight of organophilic clay of the amine-modified montmorillonite type, 0.1% to 20% by weight of plasticizer, 5% to 85% by weight of a solvent-diluent system, 0 to 10% (preferably 0% or between 1% and 10%) by weight of pigment or dye, and 0 to 10% (preferably 0% or between 0.1% and 10%) by weight of usual additives, the sum of the percentages being equal to 100.

The nail varnishes according to the invention can be obtained by the abovementioned technology, namely by mixing a colourless thixotropic nitrocellulose gel and a nonthixotropic colourless base, which makes it possible to obtain a colourless thixotropic nitrocellulose antisedimenting base, which is a colourless nail varnish, to which pigments and/or dyes are optionally added if the invention is to obtain a coloured-nail varnish. According to the invention, in this process, all or part of the film forming resin usually employed is replaced with an arylsulphonylurethane, especially with the abovementioned new arylsulphonylurethanes according to the invention.

The following nonlimiting examples illustrate the invention and the advantages which it provides.

EXAMPLE 1

Tosylurethane of a glycerol polyethertriol with a mass of 400

This compound is obtained by reaction of tosyl isocyanate of the formula

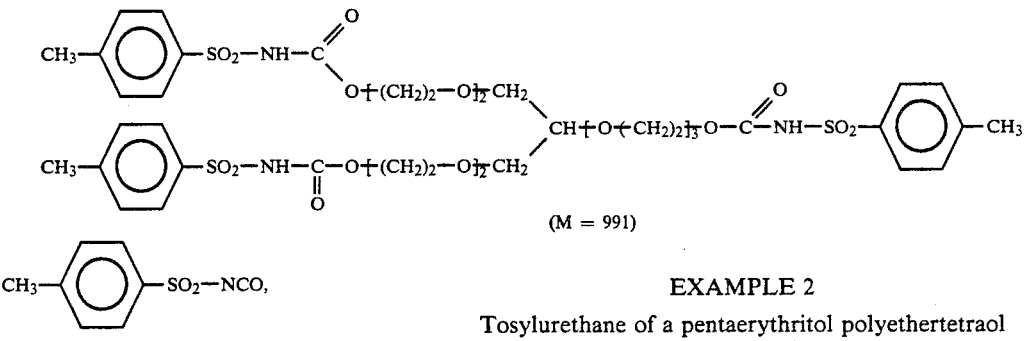

which is an industrial commercial product, with the glycerol polyethertriol with a weight of 400, of the following formula:

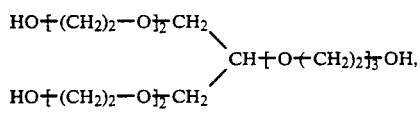

a commercial product which can be obtained by reaction between glycerol and ethylene oxide.

A jacketed 1-1 reactor is employed. The temperature is controlled with the aid of circulating oil. Probes make it possible to measure the temperature of the oil and that of the reaction mixture. The reaction is carried out under a gentle stream of nitrogen. The reactor carries above it a dropping funnel containing 140.8 g of tosyl isocyanate, nitrogen being delivered onto the isocyanate, and a condenser as well as a mechanical stirrer which makes it possible to homogenise the reaction mixture. The alcohol (96.1 g), in which the hydroxyl functional group content is 7.43 eq/kg, is placed in the reactor. The initial temperature of the oil bath is set at 30° C. and the isocyanate is then added dropwise while the temperature of the oil bath is raised as a function of the viscosity of the mixture so as to prevent its solidification. Once the addition is finished, stirring is continued until all the isocyanate disappears while the temperature is raised by approximately 10° C. Monitoring of the residual isocyanate is performed by determination in samples of the mixture. The total reaction time is approximately 1.5 h and the maximum temperature reached is close to 60° C. The product (237 g), which is in the form of a whitish resin, is then poured. At room temperature (approximately 20° C.) this resin is a very viscous liquid. The GPC (gel permeation chromatography) chromatogram with twin UV and refractometry detection shows that the reaction product is the only one and that the reaction is quantitative.

IR and $^1$H NMR spectra show, furthermore, that the resin has the structure:

(M = 991)

EXAMPLE 2

Tosylurethane of a pentaerythritol polyethertetraol with a mass of 576

The operation is as in Example 1, 104.6 g of the polyethertetraol with a mass of 576 and of the following formula:

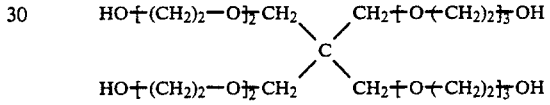

being used in place of the glycerol polyethertriol.

This polyethertetraol is a commercial product which can be obtained by reaction between the pentaerythritol and ethylene oxide. The experimental content of hydroxyl functional groups of the compound employed is 6.54 eq/kg.

135 g (0.685 mol) of tosyl isocyanate are also employed.

The total reaction time is approximately 1.3 h and the maximum temperature reached approximately 96° C. At this temperature the product obtained (239.6 g) is in the form of a translucent resin. At room temperature (approximately 20° C.) it is in the form of a hard, uncrystallised but slightly sticky solid.

Analysis by GPC shows that the reaction product is the only one and that the reaction is quantitative.

IR and $^1$H NMR spectra show that this resin has the structure:

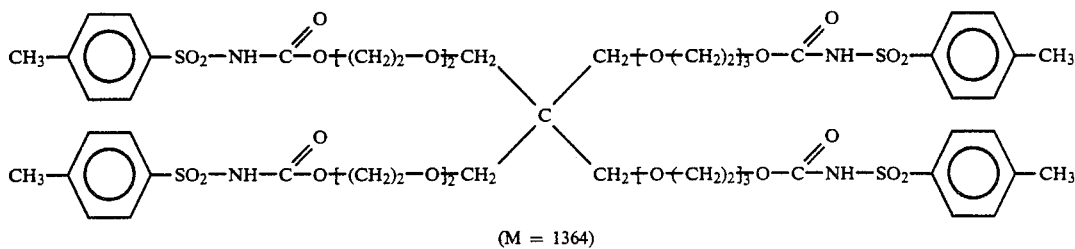

(M = 1364)

EXAMPLE 3

Tosylurethane of a pentaerythritol polyethertetraol with a mass of 356

The operation is carried out as in Example 1, 61.86 g of the polyethertetraol with a mass of 356, of the following formula:

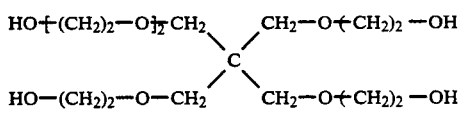

being employed in place of the glycerol polyethertriol.

This polyethertetraol is a commercial product which can be obtained by reaction between pentaerythritol and ethylene oxide. The product employed has an experimental content of hydroxyl functional groups of 11.01 eq/kg.

135 g of tosyl isocyanate are also employed.

The total reaction time is approximately 3.25 h and the maximum temperature reached approximately 103° C. At room temperature the product obtained (196.8 g) is in the form of an opaque and hard, white crystalline solid.

Analysis by GPC shows that the product is the only one and that the reaction is quantitative.

IR and $^1$H NMR spectra show that its structure is the following:

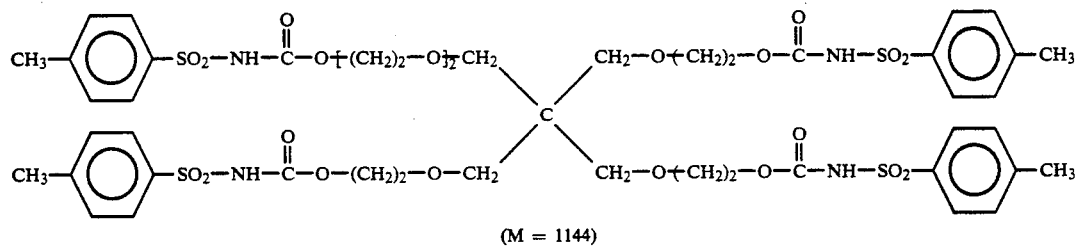

(M = 1144)

EXAMPLE 4

Tosylurethane from 2-ethoxyethanol

The operation is carried out as in Example 1, 70.39 g of 2-ethoxyethanol, in which the hydroxyl content is 11.09 eq/kg, in place of the polyethertriol.

154 g of tosyl isocyanate are also employed.

The total reaction time is approximately 3.5 h and the maximum temperature reached approximately 70° C. At this temperature the product obtained (224 g) is a translucent and very viscous liquid. At room temperature (approximately 20° C.) it is a white, opaque and soft crystalline solid.

Analysis by GPC shows that the product is the only one and that the reaction is quantitative.

IR and $^1$H NMR spectra show that its structure is the following:

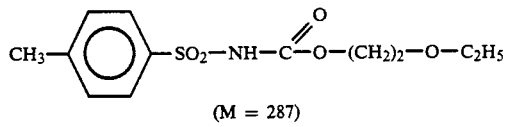

(M = 287)

EXAMPLE 5

Tosylurethane from trioxyethylene glycol

The operation is carried out as in Example 1, 64.41 g of trioxyethylene glycol OH—[—(CH$_2$)$_2$—O—]$_3$H, in which the hydroxyl content is 13.32 eq/kg, being employed in place of the polyethertriol.

169.2 g of tosyl isocyanate are also employed.

The total reaction time is approximately 5.5 h and the maximum temperature reached approximately 95° C. At room temperature (approximately 20° C.) the product obtained (233 g) is in the form of a translucent, colourless, brittle and very slightly viscous solid.

Analysis by GPC shows that the product is the only one and that the reaction is quantitative.

IR and $^1$H NMR spectra show that its structure is the following:

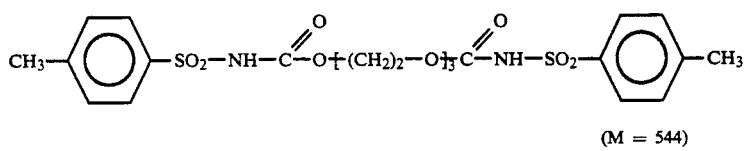

(M = 544)

EXAMPLE 6

Tosylurethane from ethanol

The operation is carried out as in Example 1, 48.05 g of ethanol, in which the hydroxyl content is 21.71 eq/kg, being employed in place of the polyethertriol.

207 g of tosyl isocyanate are also employed.

The total reaction time is approximately 1.6 h and the maximum temperature reached is approximately 53° C. However, to pour the product (255 g), it must be heated to approximately 83° C. At room temperature (approximately 20° C.) the product obtained is a white crystalline solid.

Analysis by GPC shows that the product is the only one and that the reaction is quantitative.

IR and $^1$H NMR spectra show that its structure is the following:

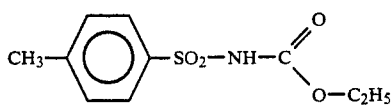

EXAMPLE 7

Tosylurethane from 1,3-propanediol

The operation is carried out as in Example 1, 33.81 g of 1,3-propanediol, in which the hydroxyl content is 26.28 eq/kg, being employed in place of the polyethertriol.

175.23 g of tosyl isocyanate are also employed.

The total reaction time is approximately 1.8 h and the maximum temperature reached approximately 96° C. At this temperature the product (209 g), is very viscous, translucent, orange in colour. At room temperature (approximately 20° C.) it is a brittle solid of orangey colour, with the structure:

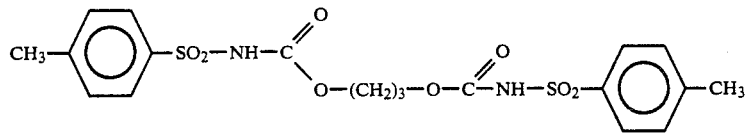

(M = 470)

EXAMPLE 8

Tosylurethane from cyclohexanol

The operation is carried out as in Example 1, 78.24 g of cyclohexanol, in which the hydroxyl content is 9.98 eq/kg, being employed in place of the polyethertriol.

154.1 g of tosyl isocyanate are also employed.

The total reaction time is approximately 3.3 h and the maximum temperature reached 76° C. At this temperature the product (232 g) appears as a translucent and colourless viscous liquid. At room temperature (approximately 20° C.) it is a translucent and colourless solid.

Analysis by GPC shows that the product is the only one and that the reaction is quantitative.

IR and $^1$H NMR spectra show that its structure is the following:

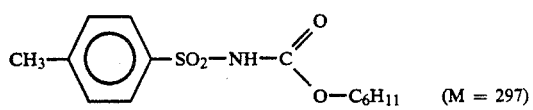 (M = 297)

EXAMPLE 9

Tosylurethane from 1-octanol

The operation is carried out as in Example 1, 88.91 g of $CH_3$—$(CH_2)_7$—OH, in which the hydroxyl content is 7.67 eq/kg, being employed instead of the polyethertriol.

134.64 g of tosyl isocyanate are also employed.

The total reaction time is approximately 3.5 h and the maximum temperature reached 78° c. At this temperature the product (223.5 g) is in the form of a translucent and colourless viscous liquid. At room temperature (approximately 20° C.) the product remains viscous.

Analysis by GPC shows that the product is the only one and that the reaction is quantitative.

IR and $^1$H NMR spectra show that its structure is the following:

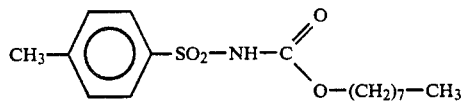

(M = 327)

EXAMPLE 10

Tosylurethane from 1-pentanol

The operation is carried out as in Example 1, 66.86 g of $CH_3$—$(CH_2)_4$—OH, in which the hydroxyl content is 11.34 eq/kg, being employed in place of the polyethertriol.

149.6 g of tosyl isocyanate are also employed.

The total reaction time is approximately 3.5 h and the maximum temperature reached 59° C. At this temperature and at room temperature (approximately 20° C.) the product (216 g) is in the form of a translucent viscous liquid, with a slight green-yellow tint.

Analysis by GPC shows that the product is the only one and that the reaction is quantitative.

IR and $^1$H NMR spectra show that its structure is the following:

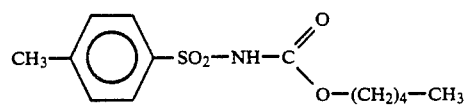

(M = 285)

EXAMPLE 11

Tosylurethane from isobutanol

The operation is carried out as in Example 1, 56.7 g of $(CH_3)_2CH$—$CH_2OH$, in which the hydroxyl content is 13.49 eq/kg, being employed in place of the polyethertriol.

150.86 g of tosyl isocyanate are also employed.

The total reaction time is approximately 5.2 h and the maximum temperature reached 56° C. At this temperature and at room temperature (approximately 20° C.) the product (207 g) is in the form of a translucent and colourless viscous liquid.

Analysis by GPC shows that the product is the only one and that the reaction is quantitative.

IR and $^1$H NMR spectra show that its structure is the following:

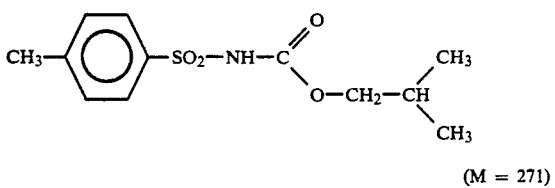

(M = 271)

EXAMPLE 12

Tosylurethane from isopropanol

The operation is carried out as in Example 1, 53.03 g of $(CH_3)_2CHOH$, in which the hydroxyl content is 16.64 eq/kg, being employed in place of the polyethertriol.

174 g of tosyl isocyanate are also employed.

The total reaction time is approximately 4.2 h and the maximum temperature reached 56° C. At this temperature the product (227 g) is a translucent viscous liquid with a slight green-yellow tint. At room temperature (approximately 20° C.) it is a white and opaque crystalline solid.

Its structure is:

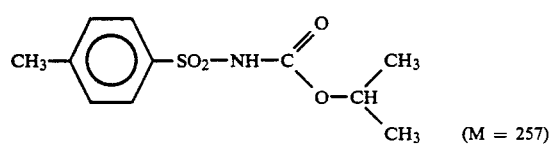

(M = 257)

EXAMPLE 13

Tosylurethane from trimethylolpropane

The operation is carried out as in Example 1, 99.21 g of

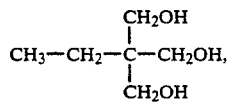

in which the hydroxyl content is 22.36 eq/k, being employed in place of the polyethertriol.

437.44 g of tosyl isocyanate are also employed.

The total reaction time is approximately 3.8 h and the maximum temperature reached 138° C. At this temperature the product (536 g) is very viscous. At room temperature (approximately 20° C.) it is a brittle and opaque solid, slightly orangy-yellow in colour.

Analysis by GPC shows that the product is the only one and that the reaction is quantitative.

IR and $^1H$ NMR spectra show that its structure is the following:

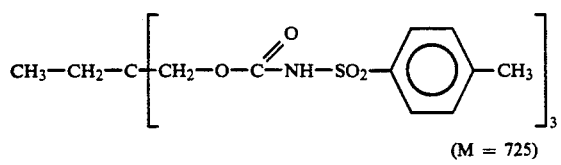

(M = 725)

EXAMPLE 14

Tosylurethane from 2-butanol

The operation is carried out as in Example 1, 65.99 g of $CH_3$—$CH_2$—$CHOH$—$CH_3$, in which the hydroxyl content is 13.49 eq/kg, being employed in place of the polyethertriol.

175.58 g of tosyl isocyanate are also employed.

The total reaction time is approximately 4.3 h and the maximum temperature reached 53° C. At this temperature and at room temperature (approximately 20° C.) the product (241 g) is in the form of a translucent viscous liquid, with a slight green-yellow tint.

Analysis by GPC shows that the product is the only one and that the reaction is quantitative.

IR and $^1H$ NMR spectra show that its structure is:

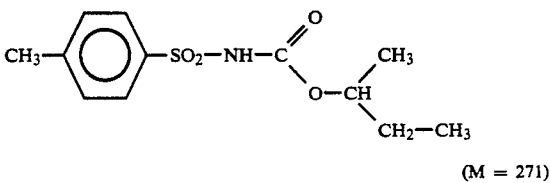

(M = 271)

EXAMPLE 15

Tosylurethane from 3-methyl-2-butanol

The operation is carried out as in Example 1, 88.15 g of $CH_3$—$CHOH$—$CH(CH_3)_2$, in which the hydroxyl content is 11.34 eq/kg, being employed in place of the polyethertriol.

197.21 g of tosyl isocyanate are also employed.

The total reaction time is approximately 4 h and the maximum temperature reached 90° C. At this temperature the product is viscous and can be easily poured. At room temperature (approximately 20° C.) it is a white crystalline solid.

Analysis by GPC shows that the product is the only one and that the reaction is quantitative.

IR and $^1H$ NMR spectra show that its structure is:

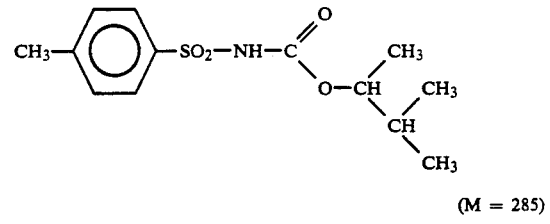

(M = 285)

EXAMPLE 16

Tosylurethane from glycerol

The operation is carried out as in Example 1, 31.32 g of glycerol, in which the hydroxyl content is 32.57 eq/kg, being employed in place of the polyethertriol.

200 g of tosyl isocyanate are also employed.

The total reaction time is approximately 4.3 h and the maximum temperature reached 135° c. At this temperature the product is a very viscous, opaque and white liquid. At room temperature (approximately 20° C.) it is a brittle, slightly yellowish crystalline solid.

Analysis by GPC shows that the product is the only one and that the reaction is quantitative.

IR and ¹H NMR spectra show that its structure is:

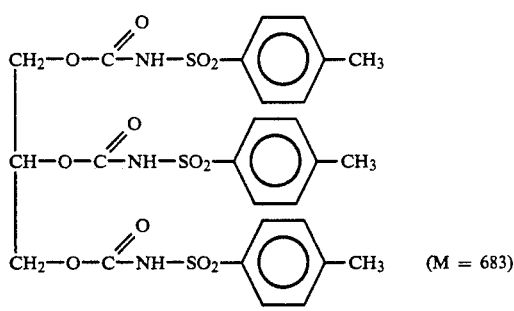 (M = 683)

EXAMPLE 17

Tosylurethane from xylitol

The operation is carried out as in Example 1, 50 g (0.332 mol) of xylitol: $CH_2OH-(CHOH)_3-CH_2OH$, being employed in place of the polyethertriol.

330 g (1.67 mol) of tosyl isocyanate are also employed.

The total reaction time is approximately 3.3 h and the maximum temperature reached is higher than 120° C.

The product obtained (380 g) is a hard brittle solid at room temperature.

Its structure is:

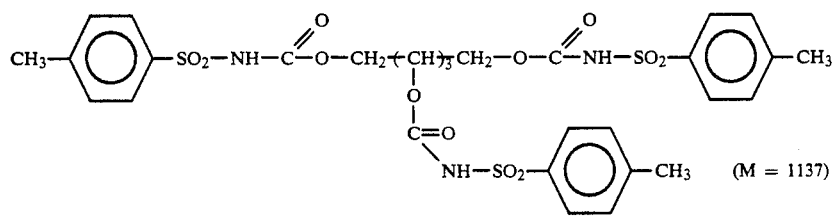 (M = 1137)

EXAMPLES 18 to 34

Nitrocellulose nail varnishes according to the invention

The varnishes of Examples 18 to 34 were produced with the tosylurethanes of Examples 1 to 17, respectively, as film forming resin. A nonthixotropic colourless base whose weight composition is the following is produced first of all merely by mixing the constituents:

| Dry nitrocellulose E28 | 12% |
| Camphor | 1.5% |
| Dibutyl phthalate | 7% |
| Film forming resin | 11.5% |
| Isopropanol | 6% |
| Ethyl acetate | 14% |

| Butyl acetate | 25% |
| Toluene | 23% |

A colourless thixotropic nitrocellolose gel whose weight composition is the following is then produced merely by mixing the constituents:

| Dry nitrocellulose type E33 | 15% |
| Camphor | 3% |
| Isopropanol | 13% |
| Ethyl acetate | 5% |
| Butyl acetate | 25% |
| Toluene | 32% |
| Dimethylbenzyldodecylammonium montmorillonite | 7% |

A colourless thixotropic nitrocellulose antisedimenting base is then produced, which is a colourless nail varnish, merely by mixing the following constituents:

20.00 parts by weight of the abovementioned colourless thixotropic nitrocellulose gel, 0.03 parts by weight of 85 % phosphoric acid, 79.97 parts by weight of the nonthixotropic colourless base corresponding to each example.

The weight composition of these 17 colourless nail varnishes is therefore the following:

| Dry nitrocellulose | 12.60% |
| Camphor | 1.80% |
| Dibutyl phthalate | 5.60% |
| Film forming resin | 9.20% |
| Isopropanol | 7.40% |
| Ethyl acetate | 12.20% |
| Butyl acetate | 24.99% |
| Toluene | 24.79% |
| Dimethylbenzyldodecylammonium montmorillonite | 1.40% |
| $H_3PO_4$ (85%) | 0.03% |

The characteristics of these colourless nail varnishes are collated in the following table, which also shows the results obtained with a colourless nail varnish of the state of the art, produced as according to Example 18, but with the film forming resin according to the invention replaced with the arylsulphonamide-formaldehyde resin marketed under the name of Santolite (comparative example).

| | Characteristics | | | | | | |
|---|---|---|---|---|---|---|---|
| | Brookfield viscosity at 20° C. - spindle No. 3 | | | | "Persoz" hardness | "Gardner" | Releasable |
| Ex. No. | 5 rev/min | 50 rev/min | 5 rev/min | Thixotrophy value | (3h) | gloss at 60° | formaldehyde content |
| 18 | 2 300 | 960 | 1 500 | 1.6 | / | 82 | <0.01% |
| 19 | 2 140 | 900 | 1 440 | 1.6 | / | / | <0.01% |
| 20 | 2 300 | 914 | 1 500 | 1.6 | 87 | 82 | <0.01% |
| 21 | 1 800 | 670 | 1 100 | 1.6 | / | 84 | <0.01% |
| 22 | 1 640 | 710 | 900 | 1.3 | 78 | 83 | <0.01% |
| 23 | 1 340 | 652 | 820 | 1.3 | / | 84 | <0.01% |

-continued

| Ex. No. | Brookfield viscosity at 20° C. - spindle No. 3 | | | Characteristics | | | |
|---|---|---|---|---|---|---|---|
| | 5 rev/min | 50 rev/min | 5 rev/min | Thixotrophy value | "Persoz" hardness (3h) | "Gardner" gloss at 60° | Releasable formaldehyde content |
| 24 | 1 540 | 768 | 980 | 1.3 | 103 | 84 | <0.01% |
| 25 | 1 340 | 652 | 900 | 1.4 | 99 | 84 | <0.01% |
| 26 | 1 320 | 636 | 900 | 1.4 | / | 82 | <0.01% |
| 27 | 1 360 | 634 | 900 | 1.4 | / | 84 | <0.01% |
| 28 | 1 500 | 644 | 900 | 1.4 | 86 | 82 | <0.01% |
| 29 | 1 400 | 650 | 900 | 1.4 | / | 83 | <0.01% |
| 30 | 4 300 | 1 320 | 1 900 | 1.4 | / | 85 | <0.01% |
| 31 | 2 200 | 940 | 1 400 | 1.5 | / | 83 | <0.01% |
| 32 | 2 180 | 920 | 1 300 | 1.4 | / | 83 | <0.01% |
| 33 | 3 180 | 1 300 | 1 800 | 1.4 | / | 86 | <0.01% |
| 34 | 2 040 | 720 | 1 100 | 1.5 | 180 | 87 | <0.01% |
| Comparative | 3 100 | 930 | 1 680 | 1.8 | 120 | 80 | 0.60% |

To determine the thixotropy value, the Brookfield viscosity is first of all measured after stirring for 1 min at 5 rev/min. Stirring is again carried out for 1 min, but at 50 rev/min, and then a second measurement is performed. Stirring is carried out again for 1 min at 5 rev/min and then a third measurement is performed. The thixotropy value is the ratio of the values obtained from the third and second measurements respectively.

To determine "Persoz" hardness, a film of varnish 150 μm in thickness is applied onto a glass plate and the measurements are then carried out with a Persoz pendulum after various drying times at 20° C. and at a relative humidity of 65%. The values shown are those obtained after drying for 3 h.

To determine "Gardner" gloss, a film of varnish 200 μm in thickness is applied onto a planar substrate, and then, after drying for more than 1 h at 20° C., a measurement is made, with the aid of a glossmeter, of the percentage of light emitted by a source onto the film of varnish at an incidence angle of 60° and reemitted by the film at this same angle. The greater the quantity of reemitted light, the more glossy is the film of varnish.

To determine the releasable formaldehyde content, a solution containing approximately 100 g/l of resin in acetone is produced first of all and the resin is then hydrolysed at approximately 80° C. after addition of an aqueous solution of dilute hydrochloric acid. The formaldehyde released is then distilled off and is then reacted with acetyl acetone in the presence of an aqueous solution of ammonium acetate. The coloured pyridine derivative formed is then determined by spectrophotometry at a wavelength of 413 nm.

In the case of Examples 18 to 29 and 34, and the comparative example, coloured nail varnishes were then produced by adding to the colourless nail varnishes 1.05% by weight of $TiO_2$ and 0.036% by weight of red organic pigment "DC Red 34" according to the nomenclature of the Food and Drug Administration (FDA).

The coloured nail varnish of Examples 23, 25 to 29, 34 and of the comparative example is then applied onto the nail (two coats) by a manicurist who checks the state of the varnish in the course of time (general appearance, flaking, wear etc.). The people whose nails are subjected to this test must have a normal and usual activity. The result, expressed in number of days for which the varnish is judged to have a satisfactory general appearance, is the following:

| | |
|---|---|
| Example 23 | 2.0 d |
| Example 25 | 2.1 d |
| Example 26 | 2.0 d |
| Example 27 | 2.3 d |
| Example 28 | 2.0 d |
| Example 29 | 2.4 d |
| Example 34 | 2.4 d |
| Comparative example | 2.3 d |

In addition, the manicurist has noted, on the one hand, that the drying time (time after which a finger no longer leaves any print on the nail varnish) is markedly improved when compared with the comparative example (3 to 7 min in the case of the examples according to the invention, instead of 8 min) and, on the other hand, that the gloss (visual assessment) is superior in the case of the examples according to the invention to that obtained for the comparative example.

Furthermore, a sedimentation test, on the one hand at 20° C. and, on the other hand, at 50° C., in bottles of the type of those in which nail varnishes are usually packaged and marketed was carried out with the coloured nail varnishes of Examples 18 to 29 and 34 and with the coloured nail varnish of the comparative example. Periodical visual checks show, both at 20° C. and at 50° C., that no deposit has formed at the bottom of the bottles after 4 months' storage in the case of all the examples according to the invention and of the comparative example.

We claim:

1. A poly(arylsulphonylurethane) of molecular weight 450–1500 of formula (II)

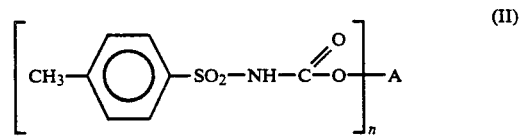

(II)

wherein n is an integer and $2 \leq n \leq 5$ and A is a di-, tri, tetra- or pentavalent organic radical, depending whether n is equal to 2, 3, 4 or 5 respectively, and A is the residue of a polyol of structure

and A is a member selected from the group consisting of polymethylene glycols, polyoxyalkylene glycols, polyethertriols, polyethertetraols, glycerol, trimethylolalkanes and xylitol.

2. A poly(arylsulphonylurethane) according to claim 1, wherein said polyethertriol has the formula

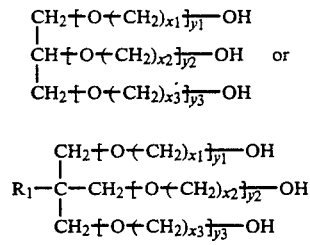

wherein $x_1$, $x_2$ and $x_3$ are the same or different and are 1, 2, 3 or 4, $y_1$, $y_2$ and $y_3$ are the same or different and are 0, 1, 2, 3, 4, 5 or 6, provided that $y_1$, $y_2$ and $y_3$ are not simultaneously zeros, $R_1$ is hydrogen or a linear or branched alkyl chain containing 1 to 8 carbon atoms or an alkyl chain containing 1 to 8 carbon atoms which is substituted by at least one alkoxy radical, and said polyethertetraol has the formula

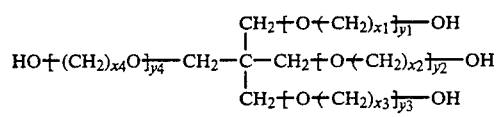

wherein $x_1$, $x_2$, $x_3$ and $x_4$ are the same or different and are 1, 2, 3 or 4, $y_1$, $y_2$, $y_3$ and $y_4$ are the same or different and are 0, 1, 2, 3, 4, 5 or 6, provided that $y_1$, $y_2$, $y_3$ and $y_4$ are not simultaneously zeros.

3. The poly(arylsulfonylurethane) according to claim 2, wherein $x_1 = x_2 = x_3 = x_4$ and $y_1 = y_2 = y_3 = y_4$.

4. A nail varnish consisting essentially of nitrocellulose, a film forming resin, a plasticizer, a gelling agent and a solvent-diluent system wherein the film forming resin includes an arylsulphonylurethane which is a member selected from the group consisting of poly(arylsulphonylurethanes) of formula (II)

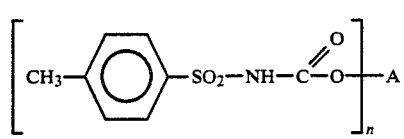

wherein n is an integer and $2 < n < 5$ and A is a di-, tri-, tetra- or pentavalent organic radical, depending whether n is equal to 2, 3, 4 or 5 respectively, and A is the residue of a polyol of structure $A(OH)_n$ and A is a member selected from the group consisting of polymethylene glycols, polyoxyalkylene glycols, polyethertriols, polyethertetraols, glycerol, trimethylolalkanes and xylitol and of mono(arylsulphonylurethanes) of formula (I)

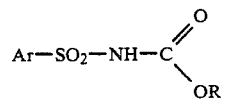

wherein

Ar is an aromatic group;

R is a linear or branched alkyl or cycloalkyl group, or an alkyl or cycloalkyl group substituted by at least one alkoxy or polyoxyalkyl group and at least one additive which is a pigment, a dye, a wetting agent, a gelling agent, a swelling agent, an Oriental essence or an agent capable of absorbing UV radiation.

5. A nail varnish according to claim 4 which consists of 5% to 20% by weight of nitrocellulose, 1% to 20% by weight of said arylsulphonylurethane, 0.1% to 5% by weight of organophilic clay of an amine-modified montmorillonite type, 0.1% to 20% by weight of a plasticizer, 5% to 85% by weight of a solvent-diluent system, 0 to 10% by weight of a pigment or dye and 0 to 10% by weight of an additive, at least one of a wetting agent for the organophilic clay and a swelling agent and an Oriental essence or an agent capable of absorbing UV radiation the percentages being equal to 100.

6. The nail varnish according to claim 4 wherein R contains 2-12 carbon atoms.

7. The nail varnish according to claim 4 wherein said mono(arylsulfonylurethane) has molecular weight of 230-350.

8. The nail varnish according to claim 4 wherein said mono(arylsulfonylurethane) is a member selected from the group consisting of

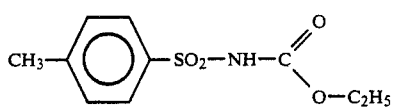
a)

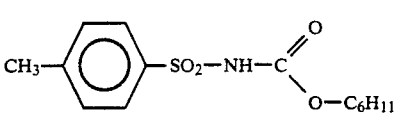
b)

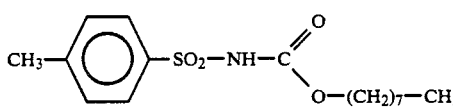
c)

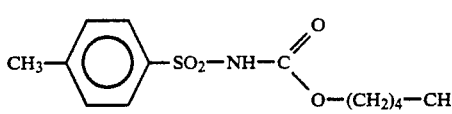
d)

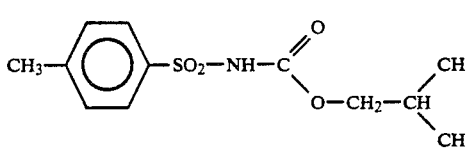
e)

and

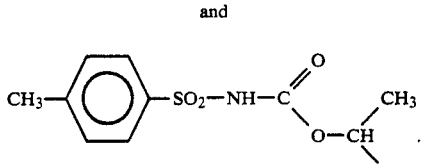

* * * * *